United States Patent
Laughland et al.

(10) Patent No.: US 8,229,763 B2
(45) Date of Patent: Jul. 24, 2012

(54) SYSTEM AND METHOD FOR ADVANCED ORDER MEDICATION MANAGEMENT

(75) Inventors: Dean William Laughland, Chicago, IL (US); Dennis Robert Dale, Warrenville, IL (US); Michael Thomas Randazzo, Cary, IL (US)

(73) Assignee: General Electric Company, Schenectady, NY (US)

( * ) Notice: Subject to any disclaimer, the term of this patent is extended or adjusted under 35 U.S.C. 154(b) by 1108 days.

(21) Appl. No.: 11/414,849

(22) Filed: May 1, 2006

(65) Prior Publication Data

US 2007/0088458 A1 Apr. 19, 2007

Related U.S. Application Data

(60) Provisional application No. 60/726,888, filed on Oct. 14, 2005.

(51) Int. Cl.
  *G06Q 10/00* (2012.01)
  *G06Q 50/00* (2012.01)
  *G06F 17/00* (2006.01)

(52) U.S. Cl. .................... 705/3; 705/2; 705/28; 700/231

(58) Field of Classification Search ................. 705/2, 3, 705/28
See application file for complete search history.

(56) References Cited

U.S. PATENT DOCUMENTS

| | | | |
|---|---|---|---|
| 5,301,105 A | 4/1994 | Cummings, Jr. | |
| 5,758,095 A * | 5/1998 | Albaum et al. | 705/2 |
| 5,924,074 A | 7/1999 | Evans | |
| 6,317,719 B1 | 11/2001 | Schrier et al. | |
| 6,347,329 B1 | 2/2002 | Evans | |
| 7,860,583 B2 * | 12/2010 | Condurso et al. | 700/2 |
| 2001/0044731 A1 * | 11/2001 | Coffman et al. | 705/3 |
| 2001/0051880 A1 | 12/2001 | Schurenberg et al. | |
| 2002/0042725 A1 | 4/2002 | Mayaud | |
| 2002/0042726 A1 | 4/2002 | Mayaud | |
| 2003/0050802 A1 | 3/2003 | Jay et al. | |
| 2003/0074225 A1 | 4/2003 | Borsand et al. | |
| 2003/0208382 A1 | 11/2003 | Westfall | |
| 2004/0006490 A1 | 1/2004 | Gingrich et al. | |
| 2004/0172295 A1 * | 9/2004 | Dahlin et al. | 705/2 |
| 2004/0199404 A1 | 10/2004 | Ripperger et al. | |
| 2004/0220829 A1 | 11/2004 | Baharav et al. | |
| 2004/0243435 A1 | 12/2004 | Williams | |
| 2005/0086008 A1 * | 4/2005 | DiGianfilippo et al. | 702/19 |
| 2005/0240441 A1 * | 10/2005 | Suzuki et al. | 705/2 |
| 2006/0122867 A1 * | 6/2006 | Eggers et al. | 705/2 |
| 2006/0149480 A1 * | 7/2006 | Lundeen | 702/19 |
| 2006/0161459 A9 * | 7/2006 | Rosenfeld et al. | 705/3 |

OTHER PUBLICATIONS http://www.hl7.org/about/hl7about.htm, About HL7, retrieved online May 1, 2006. (10 pages).

\* cited by examiner

*Primary Examiner* — Scott Zare
(74) *Attorney, Agent, or Firm* — Hanley, Flight & Zimmerman, LLC

(57) ABSTRACT

Certain embodiments of the present invention provide a system for medication management including an order entry component and a pharmacy component. The order entry component is capable of writing an advanced order. The advanced order includes one or more related at least one of sub-orders and additives. The pharmacy component is capable of automatically processing the advanced order. The processing occurs without the intervention of a user.

16 Claims, 2 Drawing Sheets

SYSTEM AND METHOD FOR ADVANCED ORDER MEDICATION MANAGEMENT

RELATED APPLICATIONS

The present application claims the benefit of U.S. Provisional Application No. 60/726,888, filed on Oct. 14, 2005, entitled "Medication Management Interface," which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to medication management. More specifically, the present invention relates to systems and methods for advanced order medication management.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. As another example, medical personnel may enter new orders for patients. Orders may include, for example, basic medication to be given to a patient and/or a procedure or exam to be conducted.

Orders may be entered or written using an order entry system such as a Computerized Provider Order Entry (CPOE) application, for example. Orders may include, for example, basic medications, lab tests, and/or procedures. For example, a user may specify 500 mg of aspirin to be administered to the patient with the order entry system. As another example, a user may write an order to schedule a procedure for a patient using CPOE. Current systems allow only simple orders such as, for example, 500 mg of aspirin to be given every 6 hours. As another example, the order entry system may be capable of allowing a user to review, change, and/or cancel existing orders; configure default rules for specifying an order; and/or provide interaction checking for medications ordered. Interaction checking may include, for example, drug-to-drug interactions, dose range warnings, drug allergies, duplicate drugs, and/or therapeutic duplication.

A Medication Administration Record (MAR) application is a tool for health care providers such as nurses. The MAR application allows a health care provider to see, monitor, and chart the administration of medication. For example, 500 mg of aspirin may be prescribed, but only 250 mg may actually have been given because the patient was not feeling as bad at the time the dosage was given. The MAR application may indicate what medication has been prescribed and when it should be administered. In addition, the MAR application may allow a user to update the status of an order, for example, the user may indicate what was actually administered.

A Pharmacy (Rx) application is utilized by a health care provider such as a pharmacist. The Rx application handles charging and dispensing medications. In addition, the Rx application may allow a user to view existing medications that have been prescribed. In current systems, a pharmacist may manually examine and/or approve an order. The pharmacist may have to manually re-enter and/or process an order with the Rx application based on comments or notations for the order.

Clinical decision support systems provide assistance to healthcare providers such as physicians. For example, clinical decision support systems can aid a physician in making decisions regarding diagnosis and/or treatment. As another example, clinical decision support systems may perform interaction checking on prescription orders for possible adverse drug interactions. A clinical decision support system may be part of a CIS and/or HIS, for example. A clinical decision support system may utilize information stored in and/or received from other systems such as RIS, CVIS, PACS, LIS, EMR, CPOE, and/or Rx, for example. Clinical decision support systems may process, for example, orders from a CPOE application and/or lab results using rules or other criteria to provide recommendations to a health care provider.

Current systems may utilize a standard protocol to link one or more systems such as CPOE, MAR, and/or Rx applications. An example of one such protocol is HL7. HL7 provides for some kinds of structured communication of coded health care information between computer applications. Standard protocols such as HL7 may provide unused and/or comment fields or segments to convey information not supported by the protocol. However, such information, since it is not part of the standard, must be manually and/or individually processed.

Current systems linking applications such as CPOE applications, MAR applications, and Rx applications, using, for example, HL7, do not provide integrated support for advanced types of orders. That is, current systems support at most simple orders that include only dosage, start day, stop day, and frequency. In contrast, an advanced order may include orders with complex combinations of additives, parts, and/or scheduling. For example, advanced orders may include sliding scales, total parenteral nutrition (TPN), fluids with additives, taper orders, and/or linked sub-orders. For example, a TPN order may include 500 mg of potassium with vitamins and amino acids, 20-percent lipids, and 10-percent fluid. As another example, an advanced order could include scheduling such as 3 mg every Monday, Wednesday, Friday, and 5 mg every Tuesday, Thursday. Advanced orders may include linked and/or related sub-orders and/or additives. For example, a taper order for Prednisone, from which a patient must be weaned, may include linked and/or related sub-orders providing for 100 mg for the first two days, and then subsequent day 10 mg less than the last dosage. As another example, a fluids with additives advanced order may include the related additives in the order for the fluids.

Current systems, to support any form of advanced order at all, require each component to be individually entered, with no relation or link between them, and/or unstructured comments to be placed in orders that must be manually read and interpreted by an end user. Such unstructured comments are un-coded and thus unusable for automatic procedures such as interaction checking or for use by the Rx system for processing and/or fulfillment. Thus, pharmacists must build the order again in their system after manually interpreting the comments.

Thus, there is a need for a system and method for advanced order medication management.

BRIEF SUMMARY OF THE INVENTION

Certain embodiments of the present invention provide a system for medication management including an order entry component and a pharmacy component. The order entry component is capable of writing an advanced order The advanced order includes one or more related at least one of sub-orders and additives. The pharmacy component is capable of automatically processing the advanced order. The processing occurs without the intervention of a user.

Certain embodiments of the present invention provide a method for medication management including generating an advanced order, communicating the advanced order, and processing automatically the advanced order. The advanced order includes one or more related at least one of sub-orders and additives. The processing occurs without the intervention of a user.

Certain embodiments of the present invention provide a computer-readable medium including a set of instructions for execution on a computer, the set of instructions including an advanced order entry routine configured to create an advanced order, a communication routine configured to communicate the advanced order, and a processing routine configured to automatically process the advanced order. The advanced order includes one or more related at least one of sub-orders and additives. The processing occurs without the intervention of a user.

Figure 1:
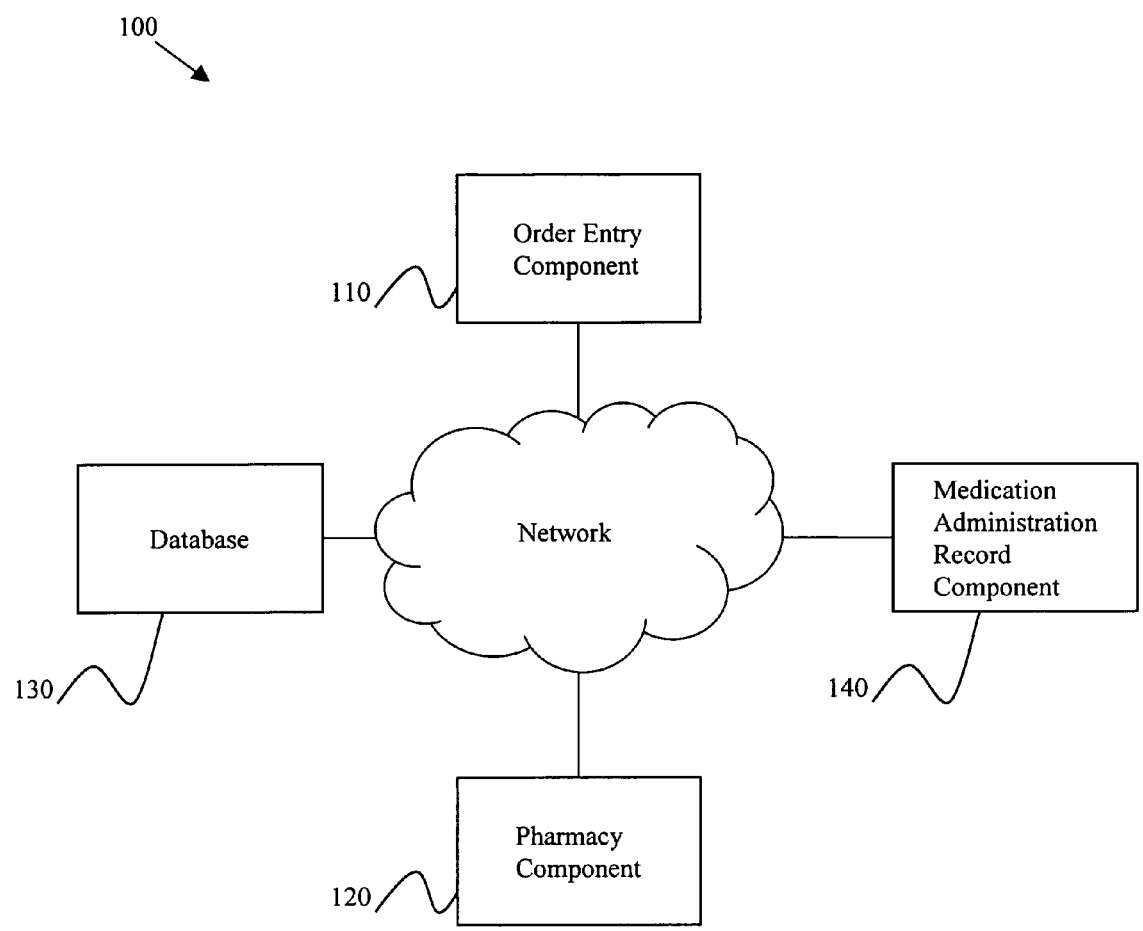
FIG. 1 illustrates a system for medication management used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a system 100 for medication management used in accordance with an embodiment of the present invention. The system 100 includes an order entry component 110 and a pharmacy component 120. In certain embodiments, the system 100 includes a database 130. In certain embodiments, the system 100 includes a medication administration record component 140.

The order entry component 110 is in communication with the pharmacy component 120. The order entry component 110 is in communication with the database 130, if present. The pharmacy component 120 is in communication with the database 130, if present. If present, the medication administration record component 140 is in communication with the order entry component 110. If present, the medication administration record component 140 is in communication with the pharmacy component 120. If present, the medication administration record component 140 is in communication with the database 130, if present.

The order entry component 110 and the pharmacy component 120 may communicate over a network, for example. Similarly, if present, the database 130 and/or medication administration record component 140 may communicate over a network, for example. The network may be or may be part of an intranet, the Internet, an HIS, an RIS, or a PACS, for example. For example, order entry component 110 and pharmacy component 110 120 may be connected to a HIS. The pharmacy component 120 may then receive data from the order entry component 110 through part of the HIS network.

The order entry component 110 may be similar to and/or include a CPOE application, as described above, for example. The pharmacy component 120 may be similar to and/or include an Rx application, as described above, for example. The medication administration record component 140 may be similar to and/or include an MAR application, as described above, for example.

In operation, an advanced order is generated and/or created. In an embodiment, the advanced order is generated by the order entry component 110. The order entry component 110 may be capable of generating advanced and simple orders, for example. In an embodiment, the advanced order is generated by the pharmacy component 120.

Advanced order may include orders with complex combinations of additives, parts, and/or scheduling. For example, advanced orders may include sliding scales, total parenteral nutrition (TPN), fluids with additives, taper orders, and/or linked sub-orders. For example, a TPN order may include 500 mg of potassium with vitamins and amino acids, 20-percent lipids, and 10-percent fluid. As another example, an advanced order could include scheduling such as 3 mg every Monday, Wednesday, Friday, and 5 mg every Tuesday, Thursday. Advanced orders may include linked and/or related sub-orders and/or additives. For example, a taper order for Prednisone, from which a patient must be weaned, may include linked and/or related sub-orders providing for 100 mg for the first two days, and then each subsequent day 10 mg less than the last dosage. As another example, a fluids with additives advanced order may include the related additives in the order for the fluids.

In an embodiment, the order entry component 110 includes one or more interfaces for generating, specifying, entering, writing, or creating an advanced order. The order entry component 110 may generated related and/or linked sub-orders and/or additives for the advanced order. For example, the order entry component 110 may include a complex dosing screen allowing a user to specify an advanced order. As another example, the order entry component 110 may include a TPN order administrator interface that allows a user to write a TPN order. As another example, the order entry component 110 may include an additives component allowing a user to define an advanced order for fluids with additives, where each additive is a linked component in the advanced order. As another example, the order entry component 110 may include an interface for specifying a taper order. The order entry component 110 may generate related and/or linked sub-orders for the taper order, for example.

The advanced order may be communicated to the pharmacy component 120. The advanced order may be communicated over a network, for example. The pharmacy component 120 receives the advanced order. The pharmacy component 120 is capable of processing the advanced order.

The pharmacy component 120 is capable of, for example, extracting complex order data from the advanced order. For example, the pharmacy component 120 may extract a TPN order from the advanced order. The pharmacy component 120 may be capable of preparing medication for a patient based at least in part on the advanced order, for example. In an embodiment, the pharmacy component 120 is capable of automatically processing the advanced order. That is, the pharmacy component 120 may, for example, perform interaction checking and/or order fulfillment without the intervention of a user such as a pharmacist when an advanced order is received.

The pharmacy component 120 may provide details of the advanced order to a pharmacist, for example. The advanced order may be prepared and/or filled by the pharmacist. Alternatively, the pharmacist may cancel or modify an advanced order using the pharmacy component 120. Modification or cancellation of an advanced order may update, modify, and/or cancel related and/or linked sub-orders or additives of the advanced order, for example. For example, if the pharmacist alters the starting dosage of a taper order, the subsequent linked sub-orders for weaning the patient may have their dosages updated and/or extended based on the new starting dosage. In an embodiment, a pharmacist may verify and/or approve an advanced order received at the pharmacy component 120. When an advanced order is available to be administered, a health care provider such as a nurse may administer the medication to a patient, for example.

Certain embodiments include database 130. If present, the database 130 is capable of storing an advanced order. That is, the database 130 is adapted to store and advanced order and linked and/or related additives and/or sub-orders. The database 130 may include other healthcare information, for example. The database 130 may be part of a RIS or HIS, for example. The database 130 may be connected to a network, for example. The database 130 may receive an advanced order. For example, the advanced order may be received from the order entry component 110. The advanced order may be received over a network, for example.

In an embodiment, the database 130 is capable of queuing a plurality of orders, including one or more advanced orders. An advanced order may be queued when, for example, the advanced order is entered by order entry component 110 but cannot be delivered to the pharmacy component 120. For example, the pharmacy component 120 may be experiencing a temporary network outage, system failure, and/or may be offline to be upgraded. The database 130 allows the advanced order to be entered and then queued until the advanced order can be delivered, received, and/or processed at a later time by the pharmacy component 120.

The medication administration record component 140 may receive an advanced order. For example, the advanced order may be received from the order entry component 110. The advanced order may be received over a network, for example.

The medication administration record component 140 is capable of processing an advanced order, including as appropriate, linked and/or related additives and/or sub-orders. The processing by the medication administration record component 140 may include, for example, presenting, displaying, monitoring, charting, and/or updating one or more advanced orders received at the medication administration record component 140. In an embodiment, the medication administration record component 140 is capable of automatically processing the advanced order. That is, the medication administration record component 140 may, for example, display, monitor, and/or chart the advanced order without the intervention of a user such as a nurse when an advanced order is received.

The medication administration record component 140 may be capable of presenting and/or displaying one or more advanced orders to a health care provider, for example. For example, the medication administration record component 140 may process an advanced order, including linked and/or related additives and/or sub-orders, to extract specific medication instructions to be displayed on a monitor or display. The medication administration record component 140 may be capable of monitoring and/or charting the administration of medication such as an advanced order, for example. For example, the medication administration record component 140 may reflect when administration was ordered and/or provided to a patient and illustrate this textually and/or graphically. The medication administration record component 140 may indicate what medication has been prescribed and when it should be administered, for example. The medication administration record component 140 may indicate what was actually administered, for example. In an embodiment, the medication administration record component 140 is capable of updating the status for an advanced order. The update of the status of the advanced order may include, for example, an indication of when and/or how much of the ordered medication was actually administered to a patient.

In certain embodiments, the system 100 includes a processing component (not shown). In an embodiment, the processing component is capable of queuing a plurality of orders, including one or more advanced orders, including related and/or linked additives and/or sub-orders. The queuing may be similar to queuing performed by the database 130, described above, for example. An advanced order may be queued when, for example, the advanced order is entered by order entry component 110 but cannot be delivered to the pharmacy component 120. For example, the pharmacy component 120 may be experiencing a temporary network outage, system failure, and/or may be offline to be upgraded. The processing component allows the advanced order to be entered and then queued until the advanced order can be delivered, received, and/or processed at a later time by the pharmacy component 120. In an embodiment, the processing component is capable of performing interaction checking on the advanced order. That is, the processing component is capable of processing an advanced order to extract information about the medication(s) ordered to determine any potential undesirable and/or harmful interactions with other ordered medications, for example. The processing component may provide interaction checking in coordination with the order entry component 110 and/or the pharmacy component 120, for example.

In an embodiment, the system 100 includes a clinical decision support component (not shown). The clinical decision support component may be capable of processing an advanced order, including linked and/or related additives and/or sub-orders. In an embodiment, the clinical decision support component is capable of automatically processing an advanced order. That is, the clinical decision support component may process the advanced order to extract information about the medication(s) ordered to determine any potential undesirable and/or harmful interactions with other ordered medications, for example. In an embodiment, the clinical decision support component is capable of performing interaction checking on the advanced order. That is, the clinical decision support component is capable of processing an advanced order to extract information about the medication(s) ordered to determine any potential undesirable and/or harmful interactions with other ordered medications, for example.

In an embodiment, one or more components of the system 100 are able to affect and/or reflect changes made to an advanced order. That is, one or more components of the system 100 may be linked with regard to the advanced order. Linked components may include, for example, the order entry component 110, the pharmacy component 120, the medication administration record component 140, the processing component and/or the clinical decision support component. For example, an advanced order may be stored in database 130. If the advanced order, including linked and/or related additives and/or sub-orders, is modified by the order entry component 110, this change may be reflected by and/or an update may be sent to one or more of the linked components, such as, for example, the medication administration record component 140 and/or the pharmacy component 120.

The components and/or functionality of system 100 may be implemented alone or in combination in hardware, firmware, and/or as a set of instructions in software, for example. Certain embodiments may be provided as a set of instructions residing on a computer-readable medium, such as a memory, CD, DVD, or hard disk, for execution on a general purpose computer or other processing device, such as, for example, a PACS workstation.

Figure 2:
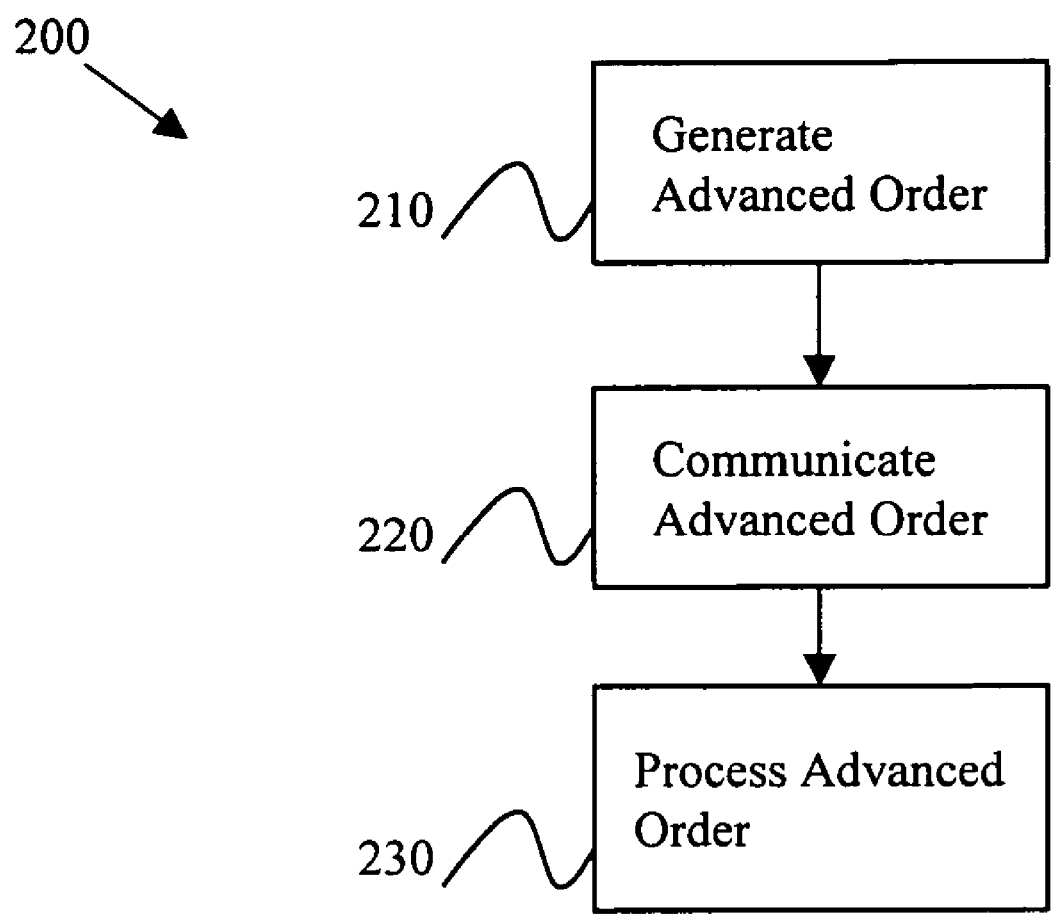
FIG. 2 illustrates a flow diagram for a method for medication management used in accordance with an embodiment of the present invention.

FIG. 2 illustrates a flow diagram for a method 200 for medication management used in accordance with an embodiment of the present invention. The method 200 includes the following steps, which will be described below in more detail. At step 210, an advanced order is generated. At step 220, an advanced order is communicated. At step 230, an advanced order is processed. The method 200 is described with reference to elements of systems described above, but it should be understood that other implementations are possible.

At step 210, an advanced order is generated. The generation of the advanced order may include the generation of linked and/or related additives and/or sub-orders. In an embodiment, the advanced order is generated by an order entry component. The order entry component may be similar to order entry component 110, described above, for example. In an embodiment, the advanced order is generated by a pharmacy component. The pharmacy component may be similar to pharmacy component 120, described above, for example. The advanced order may be generated based at least in part on input from a user or automatically, for example. For example, the advanced order may be entered by a physician using order entry component 110. As another example, the advanced order may be generated automatically in response to some condition. For example, the advanced order may be created automatically when a medication must be given as part of a scheduled procedure.

At step 220, an advanced order is communicated. The advanced order communicated may be the advanced order generated at step 210, described above, for example. Communication of the advanced order may include communication of linked and/or related additives and/or sub-orders. The advanced order may be communicated between order entry component 110 and pharmacy component 120, for example. As another example, the advanced order may be communicated between order entry component 110 and medication administration record component 140. The advanced order may be communicated over a network, for example.

In an embodiment, the advanced order is communicated at least in part using a standard protocol. That is, a standard protocol may be used, at least in part, to communicate the advanced order. The standard protocol may provide for unused or user-defined fields, segments, and/or features that may be defined, adjusted, extended, and/or modified to facilitate communicating the advanced order, for example. The protocol may be, for example, the HL7 protocol.

In an embodiment, the communication of the advanced order includes queuing the advanced order. In an embodiment, the advanced order is queued by database 130. In an embodiment, the advanced order is queued by a processing component. The advanced order may be queued when, for example, the advanced order is entered by order entry component 110 but cannot be delivered to the pharmacy component 120. For example, the pharmacy component 120 may be experiencing a temporary network outage, system failure, and/or may be offline to be upgraded. The advanced order may be entered and then queued until the advanced order can be delivered, received, and/or processed at a later time by the pharmacy component 120.

At step 230, an advanced order is processed. Processing of the advanced order may include processing of related and/or linked additives and/or sub-orders. The advanced order processed may be the advanced order generated at step 210, described above, for example. The advanced order processed may be the advanced order communicated at step 220, described above, for example.

The advanced order may be processed by a pharmacy component, database, medication administration record component, processing component, and/or clinical decision support component, for example. The pharmacy component may be similar to pharmacy component 120, described above, for example. The database may be similar to database 130, described above, for example. The medication administration record component may be similar to medication administration record component 140, described above, for example. The processing may include, for example, extracting complex order data from the advanced order, preparing medication for a patient based at least in part on the advanced order, performing interaction checking on the advanced order, presenting and/or displaying the advanced order and/or related information to a user, updating the status of the advanced order, and/or queuing the advanced order.

In an embodiment, the advanced order is processed automatically. That is, the processing of the advanced order may occur without the intervention of a user. For example, the pharmacy component 120 may perform interaction checking and/or order fulfillment without the intervention of a user such as a pharmacist when an advanced order is received.

In an embodiment, the advanced order is stored in a database. The database may be similar to database 130, described above, for example. The database may be part of a RIS or HIS, for example.

In an embodiment, interaction checking is performed automatically on the advanced order. That is, the advanced order may be processed to extract information about the medication(s) ordered to determine any potential undesirable and/or harmful interactions with other ordered medications, for example. The interaction checking may include interaction checking on one or more linked and/or related additives and/or sub-orders. The interaction checking may be performed by, for example, an order entry component, pharmacy component, processing component, and/or clinical decision support component. The order entry component may be similar to order entry component 110, described above, for example. The pharmacy component may be similar to pharmacy component 120, described above, for example. The processing component may be similar to the processing component, described above, for example. The clinical decision support component may be similar to the clinical decision support component, described above, for example.

In an embodiment, the status of the advanced order is updated. Updating the status of the advanced order may include updating the status of related and/or linked additives and/or sub-orders. The update of the status of the advanced order may include, for example, an indication of when and/or how much of the ordered medication was actually administered to a patient. Updating the status of the advanced order may include updating the status of related and/or linked additives and/or sub-orders. The status of the advanced order may be updated with a medication administration record component, for example. The medication administration record component may be similar to the medication administration record component 140, described above, for example.

As an example, in an embodiment, a user may enter a Prednisone taper order using the order entry component 110. The order entry component 110 may provide an interface for complex scheduling, for example. The user may select multiple schedules for the taper order and specify varying dosages that start off high (e.g., 250 mg) and then gradually lower the dosage over time. For example, 12 sub-orders may be generated for this taper advanced order. The order entry component 110 may then generate the advanced order and the linked sub-orders. The advanced order and linked sub-orders may then be communicated to the pharmacy component 120, the database 130, and the medical administration record component 140. The pharmacist may then use the pharmacy component 120 to update the order, which in turn appropriately updates the linked sub-orders. The pharmacist may then fill the advanced order. A nurse administering the dosage may then use the medical administration record component 140 to update the status of the advanced order and appropriate sub-orders as the dosages are administered. At any point, and potentially from any of the components of system 100, the dosage may be, for example, modified and/or cancelled, and the advanced order and linked sub-orders would be updated appropriately.

One or more of the steps of the method 200 may be implemented alone or in combination in hardware, firmware, and/or as a set of instructions in software, for example. Certain embodiments may be provided as a set of instructions residing on a computer-readable medium, such as a memory, CD, DVD, or hard disk, for execution on a general purpose computer or other processing device, such as, for example, a PACS workstation.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for medication management, the system including:

an order entry component configured to write a plurality of advanced orders, each of the plurality of advanced orders comprising a combination of linked sub-orders;

a processing device configured to implement a pharmacy component, the pharmacy component configured to automatically process the plurality of advanced orders without a manual intervention to check for undesirable interaction with respect to at least one of the plurality of advanced orders based on clinical decision support information regarding medication included in the at least one of the plurality of advanced orders and the combination of linked sub-orders associated with the at least one of the plurality of advanced orders and to prepare medication for a patient; and a database configured to:

receive the plurality of advanced orders from the order entry component;

store the plurality of advanced orders; and communicate the plurality of advanced orders to the pharmacy component for fulfillment without manual intervention, wherein one of the plurality of advanced orders includes a taper order and another one of the plurality of advanced orders includes an order automatically generated in response to a clinical procedure scheduled for the patient, the scheduled procedure to involve a medication to be given to the patient in conjunction with the clinical procedure.

2. The system of claim 1, wherein at least one of the plurality of advanced orders further includes at least one of sliding scales, total parenteral nutrition, and fluids with additives.

3. The system of claim 1, wherein the database is configured to queue the plurality of advanced orders.

4. The system of claim 1, further including a medication administration record component configured to display and to update a status of the plurality of advanced orders.

5. The system of claim 1, further including a clinical decision support component configured to automatically process the plurality of advanced orders.

6. The system of claim 1, wherein the pharmacy component is further configured to process at least one of the plurality of advanced orders and responsively prepare a patient medication.

7. The system of claim 1, wherein one of the plurality of advanced orders includes an order with multiple schedules.

8. The system of claim 1, further comprising a clinical decision support component configured to determine an undesirable interaction of one of the plurality of advanced orders with another ordered medication.

9. A computer-implemented method for medication management, the method including:

generating, with a processing device, a plurality of advanced orders including a taper order and an order automatically generated in response to a clinical procedure scheduled for a patient, the scheduled procedure to involve a medication to be given to the patient in conjunction with the clinical procedure, wherein each advanced order comprises a combination of linked sub-orders;

communicating, with a processing device, the plurality of advanced orders with a database;

storing, with a processing device, the plurality of advanced orders in the database; and processing automatically, with a processing device, the plurality of advanced orders without a manual intervention to check for undesirable interaction with respect to at least one of the plurality of advanced orders based on clinical decision support information regarding medication included in the at least one of the plurality of advanced orders and the combination of linked sub-orders associated with the at least one of the plurality of advanced orders and to prepare medication for the patient.

10. The method of claim 9, wherein the plurality of advanced orders is generated by a pharmacy component.

11. The method of claim 9, further including queuing the plurality of advanced orders.

12. The method of claim 9, further including checking automatically for an interaction checking with one of the plurality of advanced orders with another ordered medication.

13. The method of claim 9, further including updating a status of one of the plurality of advanced orders with a medication administration record component.

14. The method of claim 9, wherein the plurality of advanced orders are communicated at least in part using a standard protocol.

15. The method of claim 14, wherein the standard protocol is HL7.

16. A non-transitory computer-readable medium including a set of instructions for execution on a computer, the set of instructions including:

an advanced order entry routine configured to create a plurality of advanced orders including a taper order and an order automatically generated in response to a clinical procedure scheduled for a patient, the scheduled procedure to involve a medication to be given to the patient in conjunction with the clinical procedure, wherein each advanced order comprises a combination of linked sub-orders;

a communication routine configured to communicate the plurality of advanced orders; and a processing routine configured to automatically process the plurality of advanced orders, without a manual intervention of a user to check for undesirable interaction with respect to at least one of the plurality of advanced orders based on clinical decision support information regarding medication included in the at least one of the plurality of advanced orders and the combination of linked sub-orders associated with the at least one of the plurality of advanced orders and to prepare medication for the patient.

* * * * *